US008558049B2

(12) United States Patent
Corradi et al.

(10) Patent No.: US 8,558,049 B2
(45) Date of Patent: Oct. 15, 2013

(54) PROCESS AND APPARATUS FOR PARA-XYLENE PRODUCTION USING MULTIPLE ADSORPTIVE SEPARATION UNITS AND MULTIPLE ADSORPTIVE BED FEED POINTS

(75) Inventors: Jason T. Corradi, Arlington Heights, IL (US); Sara A. Williams, Chicago, IL (US); Stanley J. Frey, Palatine, IL (US)

(73) Assignee: UOP LLC, Des Plaines, IL (US)

( * ) Notice: Subject to any disclaimer, the term of this patent is extended or adjusted under 35 U.S.C. 154(b) by 83 days.

(21) Appl. No.: 13/326,961

(22) Filed: Dec. 15, 2011

(65) Prior Publication Data

US 2013/0158331 A1   Jun. 20, 2013

(51) Int. Cl.
   *C07C 7/12* (2006.01)
(52) U.S. Cl.
   USPC .............................. 585/826; 585/828; 585/910
(58) Field of Classification Search
   None
   See application file for complete search history.

(56) References Cited

U.S. PATENT DOCUMENTS

| 4,039,599 | A | 8/1977 | Gewartowski |
| 5,177,295 | A | 1/1993 | Oroskar et al. |
| 5,763,714 | A | 6/1998 | Hickey et al. |
| 6,369,287 | B1 | 4/2002 | Magne-Drisch et al. |
| 7,687,674 | B2 | 3/2010 | Wegerer |
| 7,915,471 | B2 | 3/2011 | Leflaive et al. |
| 7,977,526 | B2 | 7/2011 | Porter |
| 8,008,536 | B2 | 8/2011 | Winter et al. |
| 2007/0149841 | A1 | 6/2007 | Lee et al. |
| 2008/0149565 | A1 | 6/2008 | Lee et al. |
| 2009/0069612 | A1 | 3/2009 | Hotier et al. |
| 2009/0234170 | A1 | 9/2009 | Lee et al. |
| 2011/0077448 | A1 | 3/2011 | Frey |

OTHER PUBLICATIONS

International Search Report and Written Opinion dated Feb. 28, 2013 for PCT/US2012/059167.

*Primary Examiner* — Tam M Nguyen
(74) *Attorney, Agent, or Firm* — Mark R Willis

(57) ABSTRACT

A process for separating para-xylene from aromatic compounds is presented. The process introduces throughout a first step-time interval a first mixed xylene stream into a first feed input on a first adsorptive separation unit comprising multiple bed lines. The process further introduces throughout the first step-time interval a second mixed xylene stream into a second feed input on the first adsorptive separation unit. During a first portion of the first step-time interval, the process introduces material from a feed stream used during the first step-time interval into a bed line not used to deliver a stream into, or withdraw a stream from, the first adsorptive separation unit during the first step time interval. During a second portion of the first step-time interval, the process introduces material from a purification zone into the feed stream used during the first step-time interval.

10 Claims, 11 Drawing Sheets

US 8,558,049 B2

PROCESS AND APPARATUS FOR PARA-XYLENE PRODUCTION USING MULTIPLE ADSORPTIVE SEPARATION UNITS AND MULTIPLE ADSORPTIVE BED FEED POINTS

FIELD OF THE INVENTION

The disclosure relates to a process for the formation and adsorptive separation of a select xylene isomer, preferably para-xylene, from a feed stream containing a mix of aromatic and non-aromatic hydrocarbons. More specifically, the disclosure relates to increasing the efficiency of para-xylene production by eliminating the need to vaporize the product stream from the isomerization process. Most specifically, the disclosure relates to a para-xylene process comprising multiple adsorptive separation units, each using a different desorbent, to eliminate fractional distillation of the isomerized product stream, where one adsorptive separation unit accepts multiple feeds, along with a material transfer configuration to facilitate such multiple feeds.

BACKGROUND OF THE INVENTION

Para-xylene, an aromatic hydrocarbon, is an important intermediate which finds wide and varied application in chemical syntheses. Upon oxidation, para-xylene yields terephthalic acid. Polyester fabrics and resins are produced from a polymer of ethylene glycol and terephthalic acid. These polyester materials are used extensively in a number of industries and are used to manufacture such items as, for example, clothing, beverage containers, electronic components, and insulating materials.

The production of para-xylene is practiced commercially in large-scale facilities and is highly competitive. Concerns exist not only about the effective conversion of feedstock through one or more of isomerization, transalkylation and disproportionation to produce para-xylene, and effective separation of para-xylene from the resultant mixture of C8 aromatic isomers, but also with the energy costs and capital costs associated with such processes.

In prior art processes, C9 aromatics are separated from the C8 aromatics, i.e. xylene isomers, by fractional distillation. This requires heating of the admixture to vaporize the C8 and lighter aromatics. A large portion of the isomerization stream must be vaporized to accomplish the C9 separation because the stream is generally composed primarily of C8 and lighter aromatics. This separation requires a substantial amount of energy and associated cost. After the C9 aromatic removal, the C8-containing stream is then recycled into the adsorptive separation unit.

Accordingly, it would be an advance in the state of the art to provide a process for the production of para-xylene, including separation and isomeric formation from an admixture of C8 aromatic isomers, that removes the need to vaporize the isomerized stream for removal of C9 aromatics, thereby lowering operational expenses, in the form of energy consumption, and capital expenditures, in the form of required processing equipment and the size of such processing equipment.

SUMMARY OF THE INVENTION

A process for separating para-xylene from a plurality of aromatic compounds is presented. The process introduces, throughout a first step-time interval, a first mixed xylene stream comprising a plurality of xylene isomers into a first feed input on a first adsorptive separation unit comprising a plurality of bed lines, wherein that first adsorptive separation unit comprises a purification zone. The process further introduces throughout the first step-time interval a second mixed xylene stream comprising a plurality of xylene isomers into a second feed input on the first adsorptive separation unit.

During a first portion of said first said step-time interval, the process introduces material from a feed stream used during the first step-time interval into a bed line not used during the first step time interval. During a second portion of said first said step-time interval, the process introduces material from the purification zone into the feed stream used during the first step-time interval.

An apparatus for separating para-xylene from a plurality of aromatic compounds is presented. The apparatus comprises a first adsorptive separation unit comprising a rotary valve comprising more than 8 tracks, where the first adsorptive unit is in fluid communication with the rotary valve. The first adsorptive separation unit comprises a first feed input and a second feed input. The apparatus further comprises a second adsorptive separation unit, and a raffinate column in fluid communication with both the first adsorptive separation unit and the second adsorptive separation unit.

DETAILED DESCRIPTION OF PREFERRED EMBODIMENTS

Figure 1:
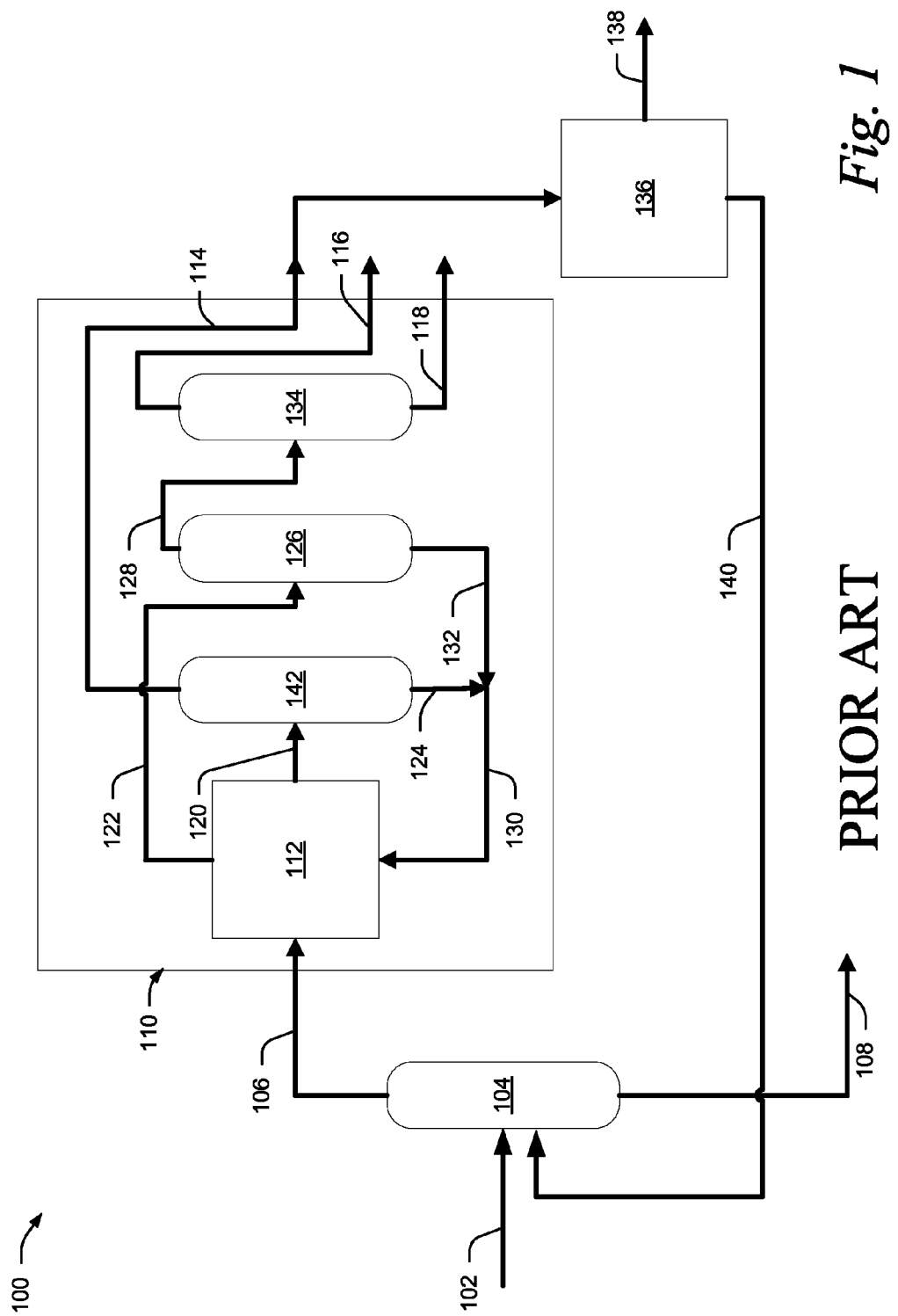
FIG. 1 is a diagram of a prior art process.

Para-xylene is typically recovered from a mixed aromatic hydrocarbon fraction derived from various sources such as catalytic reforming by liquid-liquid extraction and/or fractional distillation. The para-xylene is commercially separated from a feed stream that typically contains all three xylene isomers, namely ortho-xylene, meta-xylene, and para-xylene. The para-xylene, or other desired isomer, is separated by either fractional crystallization or adsorptive separation or a combination of these two techniques. Adsorptive separation is generally preferred as it has a significantly higher single pass recovery (~97%) relative to crystallization separation (~65%).

A typical adsorptive separation process first involves the separation of C8 aromatic hydrocarbons, including ortho-xylene, meta-xylene, para-xylene, and ethylbenzene, from heavier aromatic hydrocarbons (i.e., C9+) and non-aromatic hydrocarbons through fractional distillation.

Those skilled in the art will appreciate that the designator "CX" refers to a compound comprising X carbon atoms, "CX+" refers to a compound comprising X or greater carbon atoms, and "CX−" refers to a compound comprising X or fewer carbon atoms.

The para-xylene isomers are then separated from the C8 isomer admixture using a simulated countercurrent moving-bed (SMB) adsorptive separation unit. This simulation is performed using established commercial technology wherein an adsorbent, commonly a solid zeolitic material, is held in place in one or more cylindrical adsorbent chambers. The positions at which the streams involved in the process enter and leave the chamber(s) are slowly shifted along the height of the chamber(s). Normally there are at least four streams (feed, desorbent, extract and raffinate) employed in this procedure and the location at which the feed and desorbent streams enter the chamber and the extract and raffinate streams leave the chamber are simultaneously shifted in the same direction at set intervals in a step-wise manner. Each shift in location of these transfer points delivers or removes liquid from a different bed within the chamber.

A typical chamber has a single line for each bed. The flow into or out of a particular line, as the case may be, is controlled by a rotary valve. The shifting of streams along the bed simulates movement of the adsorbent in a direction opposite the flow of liquid, even though the adsorbent is fixed in place within the chamber. SMB chambers are also well suited for high volume production because the input and output streams have nearly constant compositions throughout simulated motion of the adsorbent material in the bed.

A typical SMB unit recycles a heavy desorbent, such as para-diethylbenzene, to separate high purity para-xylene from the other C8 isomers. Para-diethylbenzene is a C10 aromatic that is separated from para-xylene by fractional distillation.

The admixture of non-para-xylene isomers from the adsorptive separation unit is subjected to catalytic isomerization to reestablish an equilibrium amount of para-xylene isomers in the admixture. In addition to para-xylene and other C8 isomers, the isomerized stream typically contains an amount of C9+ aromatics, which will accumulate in the desorbent and, therefore, must be removed.

Processes for isolating a desired isomer of xylene without the vaporization of the full isomerized product stream are presented. The process comprises two adsorptive separation units. The first unit utilizes a heavy desorbent and the second unit utilizes a light desorbent. Those skilled in the art will appreciate that a desorbent used in combination with a simulated moving bed adsorbent system facilitates removal of an adsorbed material from the adsorbent bed. This being the case, a useful desorbent will have an affinity for the desired material, i.e., para-xylene, that is substantially the same as the affinity of the adsorbent bed for that desired material.

As used herein, the terms heavy and light are generally in reference to the boiling point of the desorbent relative to the C8 aromatics, namely, ortho-, meta-, para xylene and ethylbenzene.

In certain embodiments, the heavy desorbent is selected from the group consisting of para-diethylbenzene, para-diisopropylbenzene, tetralin, and the like, and combinations thereof. In certain embodiments, toluene and the like can be used as the light desorbent. The para-diethylbenzene has a higher boiling point than the C8 aromatic isomers and, as such, the para-diethylbenzene is the bottoms (i.e., heavy) product when separated from the C8 isomers in a fractional distillation column. Similarly, toluene has a lower boiling point than the C8 aromatic isomers and, as such, the toluene is the overhead (i.e., light) product when separated from the C8 isomers in a fractional distillation column.

Unlike prior art processes. Applicant's process comprises feeding a stream of material containing a desired xylene isomer formed in an isomerization unit into a second adsorptive separation unit, as opposed to being fed back into a fractional distillation column. An extract stream from the second adsorptive separation unit, rich in the desired xylene isomer, is fed back into a first adsorptive separation unit for isolation of the desired xylene isomer. The process is presented in greater detail below.

Referring to FIG. 1, a diagram 100 of a prior art process for the production of para-xylene is depicted. A feed stream 102 enters a xylene fractionation unit 104. The feed stream typically contains ortho-, meta-, and para-xylene isomers and may also contain quantities of ethylbenzene, toluene, C8 cycloalkanes, alkanes, and hydrocarbons having more than eight carbon atoms per molecule.

The xylene fractionation unit 104 is a fractional distillation column. The xylene fractionation unit 104 divides the incoming stream into an overhead stream 106 comprising the C8 and lighter aromatics, including the xylene isomers, ethylbenzene, and toluene, and a bottoms 108 and one or more side cut streams (not shown) comprising C9+ aromatics.

Table 1 recites an example composition for feed stream 102.

TABLE 1

| Component | Amount |
|---|---|
| para-xylene | 10-20 wt % |
| Total C8 Aromatics | 25-60 wt % |
| ethylbenzene | 10-20 wt % |
| toluene | 0.5-2.0 wt % |
| C9+ | 25-30 wt % |
| Nonaromatic hydrocarbons | <0.5 wt % |
| Nitrogen | 1.0 mg/kg |
| Sulfur | 1.0 mg/kg |

The overhead stream 106 enters the separation assembly 110, where the input stream 106 is separated into a raffinate stream 114, a toluene stream 116, and a para-xylene stream 118. The raffinate stream 114 has been substantially depleted of para-xylene but contains other C8 aromatics, including ortho-xylene, meta-xylene and ethylbenzene.

Within the separation assembly 110, the stream 106 enters an adsorptive separation unit 112. The adsorptive separation unit 112 separates the incoming stream 106 into a raffinate stream 120 and an extract stream 122. The adsorptive unit 112 typically comprises two SMB chambers and a rotary valve. Each individual chamber typically has 12 beds. A bed line connects each bed to the rotary valve. The rotary valve controls the flow of material into or out of each SMB chamber in a step-wise manner to create a simulated moving bed.

A heavy desorbent, typically para-diethylbenzene, is used to facilitate the separation of the raffinate stream 120 and extract stream 122. The raffinate stream 120 comprises ethylbenzene, meta-xylene, and ortho-xylene diluted with desorbent and any heavies. Heavies are hydrocarbons with a boiling point greater than that of the C8 aromatic isomers and include C9+ aromatics. The extract stream 122 comprises para-xylene diluted with desorbent and light ends. Light ends are hydrocarbons with a boiling point below that of the C8 aromatic isomers and include toluene and other C7− aromatics.

The raffinate stream 120 is directed to a raffinate column 142. The raffinate column 142 is a fractional distillation column that divides the incoming stream 120 into (i) an overhead raffinate stream 114 comprising ethylbenzene, meta-xylene, and ortho-xylene and (ii) a bottoms stream 124 comprising desorbent and any heavies. The bottoms stream 124 is recycled back to the adsorptive unit 112 through combined stream 130. The overhead raffinate stream 114 is directed to an isomerization unit 136.

The extract stream 122, comprising xylene isomers and ethylbenzene, enters extract column 126. Extract column 126 is a fractional distillation column that divides the incoming stream 122 into (i) an overhead stream 128 comprising para xylene and toluene and (ii) a bottoms stream 132 comprising desorbent and heavies. The bottoms stream 132 containing desorbent is recycled back to the adsorptive unit 112 through combined stream 130. Heavies in the combined desorbent stream 130 may be removed by directing a slipstream of the desorbent into a small desorbent rerun column.

The overhead stream 128, comprising para-xylene and toluene, enters finishing column 134. Finishing column 134 is a fractional distillation column that divides the incoming stream 128 into (i) an overhead toluene stream 116 and (ii) a bottoms para-xylene stream 118. The bottoms para-xylene stream 118 contains the final desired product.

The raffinate stream 114 comprising ethylbenzene, meta-xylene, and ortho-xylene enters an isomerization unit 136. Catalysts in the isomerization unit 136 reestablish an equilibrium mixture of the ortho-, meta-, and para-xylene isomers and convert the ethylbenzene into xylenes and/or benzene.

Nonaromatic compounds in the raffinate stream 114 are cracked to light ends and removed in stream 138 along with any benzene. The isomerization process also creates quantities of C9+ aromatics. The output stream 140 comprises an equilibrium mixture of xylene isomers as well as quantities of C9 aromatics and unreacted ethylbenzene. The output stream 140 is recycled back into the xylene fractionation unit 104.

The C9 aromatics produced during isomerization are separated from the C8 isomers in the xylene fractionation unit 104. While the C9 aromatics are only a very small portion of the stream, the entire C8 fraction must be vaporized to accomplish this separation.

Figure 2:
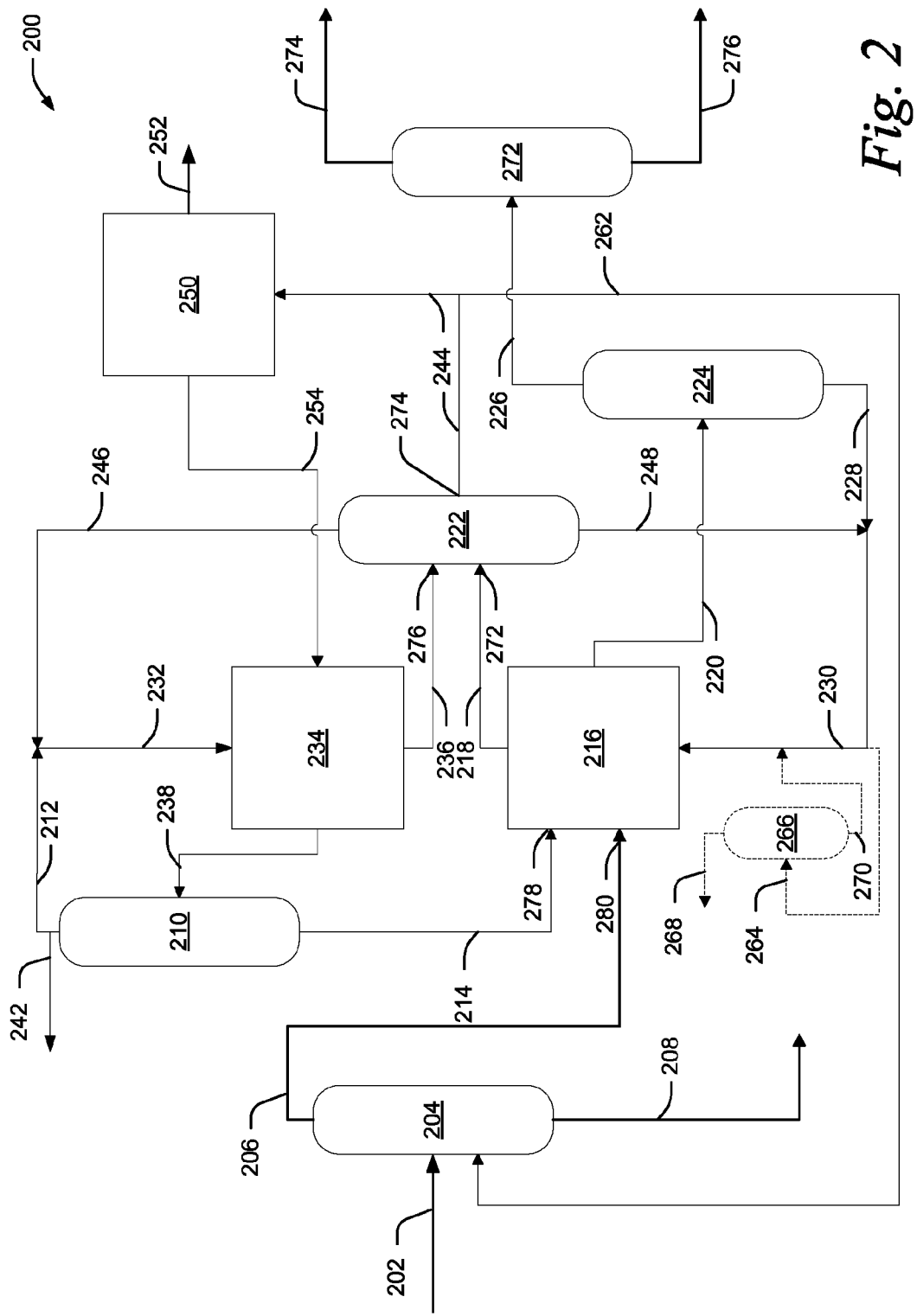
FIG. 2 is a diagram of one embodiment of the disclosed process having an adsorption unit with multiple feeds where a drag stream is fed into the xylene fractionation column.

FIG. 2 illustrates embodiment 200 of Applicant's apparatus and process. A feed stream 202 enters a xylene fractionation unit 204. In one embodiment, the feed stream 202 contains ortho-, meta-, and para-xylene isomers. In one embodiment, the feed stream 202 contains quantities of ethylbenzene, toluene, C8 cycloalkanes, alkanes, and hydrocarbons having more than eight carbon atoms per molecule.

In one embodiment, the feed stream 202 is a result of hydrotreating naphtha to remove any sulfur and nitrogen contaminants and the subsequent catalytic reforming where paraffins and naphthenes in the decontaminated naphtha are converted to aromatics. The most light ends and C7+ fractions are removed in a debutanizer and fractional distillation column, respectively. The feed stream 202, comprising a C8+ fraction, enters the xylene fractionation unit 204. In one embodiment, the feed stream 202 comprises about 23 weight percent para-xylene.

The xylene fractionation unit 204 is a fractional distillation column. The xylene fractionation unit 204 divides the incoming stream into an overhead stream 206 comprising the C8+ aromatics, including the xylene isomers, ethylbenzene, and toluene, and a bottoms stream 208 and one or more side cut streams (not shown) comprising C9+ aromatics present in the feed stream 202.

The overhead stream 206 and bottoms stream 214 from extract column 210 enter adsorptive separation unit 216 at a first feed input 278 and a second feed input 280, respectively. Adsorptive separation unit 216 separates the incoming streams 206 and 214 into a raffinate stream 218 and an extract stream 220. In one embodiment, the heavy desorbent para-diethylbenzene is used to facilitate the separation of the raffinate stream 218 and extract stream 220. In certain embodiments, the heavy desorbent is selected from the group consisting of para-diethylbenzene, para-diisopropylbenzene, tetralin, and the like, and combinations thereof. The raffinate stream 218 comprises ethylbenzene, meta-xylene, and ortho-xylene diluted with desorbent. The extract stream 220 comprises para-xylene diluted with desorbent.

In one embodiment, adsorptive unit 216 comprises an SMB assembly and a rotary valve. In other embodiments, the adsorption separation unit 216 comprises an SMB assembly and one or more rotary valves, one or more computing device operated valves, or a combination thereof. In one embodiment, the SMB assembly comprises a single physical chamber. In one embodiment, the physical chamber includes 24 beds. In one embodiment, the physical chamber includes less than 24 beds. In one embodiment, the SMB assembly includes two physical chambers. In one embodiment, each physical chamber includes 12 beds. In one embodiment, each physical chamber includes less than 12 beds. In one embodiment, each physical chamber includes more than 12 beds. In one embodiment, the physical chambers have an unequal number of beds. A bed line connects each bed in the SMB assembly to the rotary valve. The rotary valve controls the flow of material into or out of the SMB assembly in a stepwise manner to create a simulated moving bed and to flush the bed lines between flows of differing materials.

In certain embodiments, the selectivity of the adsorbent in the adsorptive separation unit 216 for C7− aromatics and light ends is very close to that of para-xylene. As such, the C7− aromatics and light ends exit the adsorptive separation unit 216 by way of extract stream 220.

The extract stream 220 enters the extract column 224. Extract column 224 is a fractional distillation column that separates the incoming stream 220 into (i) an overhead para-xylene stream 226 comprising para-xylene, C7− aromatics, and light ends and (ii) a bottoms stream 228 comprising a heavy desorbent fraction, such as para-diethylbenzene, a C10 aromatic. The bottoms stream 228 is recycled back to the adsorptive separation unit 216 through combined stream 230.

Light desorbent enters adsorptive separation unit 234 by way of combined stream 232. Adsorptive separation unit 234 separates an incoming stream 254 into a raffinate stream 236 and an extract stream 238. Stream 254 is an isomerized stream from isomerization unit 250 comprising an equilibrium mixture of xylene isomers.

In one embodiment, the light desorbent toluene is used to facilitate the separation of the raffinate stream 236 and extract stream 238. In another embodiment, a light desorbent other than toluene is used to facilitate the separation of the raffinate stream 236 and extract stream 238. The raffinate stream 236 comprises ethylbenzene, meta-xylene, and ortho-xylene diluted with desorbent. The extract stream 238 comprises para-xylene diluted with desorbent.

In one embodiment, adsorptive unit 234 comprises an SMB assembly and a rotary valve. In other embodiments, the adsorption separation unit 234 comprises an SMB assembly and one or more rotary valves, one or more computing device operated valves, or a combination thereof. In one embodiment, the SMB assembly comprises a single physical chamber. In one embodiment, the physical chamber includes 24 beds. In one embodiment, the physical chamber includes less than 24 beds. In one embodiment, the SMB assembly includes two physical chambers. In one embodiment, each physical chamber includes 12 beds. In one embodiment, each physical chamber includes less than 12 beds. In one embodiment, each physical chamber includes more than 12 beds. In one embodiment, the physical chambers have an unequal number of beds. A bed line connects each bed in the SMB assembly to the rotary valve. The rotary valve controls the flow of material into or out of the SMB assembly in a stepwise manner to create a simulated moving bed and to flush the bed lines between flows of differing materials.

The raffinate stream 236 enters a raffinate column 222 at a third location 276.

The extract stream 238 is fed into extract column 210, a fractional distillation column. Extract column 210 separates the para-xylene product in the extract stream 238 from the light desorbent, such as toluene. The overhead stream 212 comprises C7− aromatics and light impurities. The bottoms stream 214 comprises C8 aromatic isomers, including para-xylene. The light desorbent is recycled in a light desorbent loop 212, 232, 238.

In one embodiment, a slipstream 242 is extracted from the overhead stream 212. In one embodiment, slipstream 242 prevents the accumulation of additional toluene introduced into the desorbent loop from the feed stream 202. In one embodiment, slipstream 242 prevents the accumulation of light impurities in the light desorbent loop. In one embodiment, slipstream 242 comprises high purity toluene. In one embodiment, slipstream 242 comprises toluene and light impurities from the feed stream 202.

Raffinate column 222 is a fractional distillation column that separates the raffinate stream 236 and 218, each comprising para-xylene depleted C8 aromatic isomers diluted with light and heavy desorbent, respectively, into a C8 aromatic isomer stream 244, a light desorbent stream 246, and a heavy desorbent stream 248. The C8 aromatic isomer stream 244 exits the raffinate column 222 at a second location 274.

The light desorbent along with any light impurities have the lowest boiling point and are, as such, extracted as a net overhead stream 246. The heavy desorbent along with any heavies have the highest boiling point and are, as such, extracted as a net bottoms stream 248. The ortho-xylene, meta-xylene, and ethylbenzene have an intermediate boiling point and are, as such, extracted at a sidecut tray. The heavy desorbent is recycled in a heavy desorbent loop 230, 220/218, 278/748.

In one embodiment, the C8 aromatic isomer stream 244 exits the raffinate column 222 at a location below that of raffinate stream 236 and above that of raffinate stream 218. In one embodiment, the raffinate stream 236 enters raffinate column 222 at a location on the column where the composition within the column 222 is similar to the composition in stream 236. In one embodiment, the raffinate stream 218 enters raffinate column 222 at a location on the column where the composition within the column 222 is similar to the composition in stream 218. As used herein, with reference to fractional distillation columns, the term "above" refers to a location in or on the column such that liquid inserted at the location will flow down toward the reference point. Similarly, the term "below" refers to a location in or on the column such that liquid inserted at the location will flow down away from the reference point.

The C8 aromatic isomer stream 244 comprising meta-xylene, ortho-xylene, and ethylbenzene enters an isomerization unit 250. Catalysts in the isomerization unit 250 reestablish an equilibrium mixture of the ortho-, meta-, and para-xylene isomers. In one embodiment, the catalyst is an ethylbenzene dealkylation catalyst, which converts ethylbenzene to a benzene co-product. In one embodiment, the catalyst is an ethylbenzene isomerization catalyst, which converts the ethylbenzene into additional xylene isomers.

Nonaromatic compounds in the C8 aromatic isomers stream 244 are cracked to light ends and removed in stream 252 along with any benzene co-product created. The isomerization process may also create small quantities of C9 and heavier aromatics. In one embodiment, the output stream 254 comprises an equilibrium mixture of xylene isomers. In one embodiment, the output stream 254 comprises small quantities of C9+ aromatics. In one embodiment, the output stream 254 comprises unreacted ethylbenzene. In one embodiment, the output stream 254 comprises about 1.5 weight percent ethylbenzene or less. The isomerized output stream 254 enters adsorptive separation unit 234.

In certain embodiments, certain C9+ aromatics may be introduced by isomerization unit 250 and accumulate in the heavy desorbent loop 230, 220/218, 228/248. In certain configurations of the raffinate column 222, any C9 aromatics will accumulate in the isomerization loop 254, 236, 244. In other configurations of the raffinate column 222, any C9 aromatics will accumulate in the heavy desorbent loop 230, 220/218, 228/248. In yet other configurations of the raffinate column 222, any C9 aromatics will accumulate in both the isomerization loop and the heavy desorbent loop.

In different embodiments, one or more drag streams are used to prevent the accumulation of C9+ aromatics in the process. In one embodiment, if accumulation occurs in the heavy desorbent loop, a drag stream 264 is withdrawn from the desorbent loop by way of stream 230. Stream 230 comprises primarily heavy desorbent along with the C9 aromatic and heavy impurities. The drag stream 264 is fed into a fractional distillation column 266, which separates the drag stream 264 into an overhead stream 268 and a bottoms stream 270. The bottoms stream 270 comprises high purity para-diethylbenzene, which is returned to the desorbent loop by way of stream 230. In one embodiment, the amount of material withdrawn in drag stream 264 is about 1 to about 20 volume percent of stream 230.

In another embodiment, if accumulation occurs in the isomerization loop (i.e., 254, 236, 244), a drag stream 262 is withdrawn from the isomerization loop by way of raffinate stream 244. Stream 244 comprises a mixture of ortho-xylene, meta-xylene, ethylbenzene along with the C9 aromatic and heavy impurities. The drag stream is fed into the xylene fractionation column 204 where substantially all C9+ aromatics are removed in bottoms 208 and the C8 aromatics are recycled back through the process, in one embodiment, the amount of material in the drag stream 262 is about 1 to about 20 volume percent of the raffinate stream 244.

In yet another embodiment, if the accumulation occurs in both the isomerization loop and the heavy desorbent loop, drag streams 262 and 264 are both used. In other embodiments, no drag streams are used. In other embodiments, the impurities are extracted by another process known in the art capable of separating C9 aromatics and heavies from para-diethylbenzene.

The finishing column 272 separates the overhead stream 226 into an overhead stream 274 comprising C7− aromatics and light ends that entered the process by way of feed stream 202 and a bottoms stream 276 comprising high purity para-xylene.

In certain embodiments, para-ethyltoluene, structurally similar to para xylene, may be introduced into the process by the isomerization unit 250. In some embodiments, the para-ethyltoluene may not be fully separated from the para-xylene in the adsorptive separation unit 216, in the extract column 224, or in the finishing column 272 and exists as in impurity in the para-xylene product stream 276. In some embodiments, the para-ethyltoluene is removed from the para-xylene product using any technique known in the art capable of separating para-ethyltoluene from a stream of para-xylene.

In one embodiment, the bottoms para-xylene stream 276 comprises about 99.2 weight percent para-xylene. In one embodiment, the bottoms para-xylene stream 276 comprises about 99.7 weight percent para-xylene. In one embodiment, the bottoms para-xylene stream 276 comprises about 99.9 weight percent para-xylene. In one embodiment, the bottoms para-xylene stream 276 comprises greater than about 99.9 weight percent para-xylene.

Figure 3:
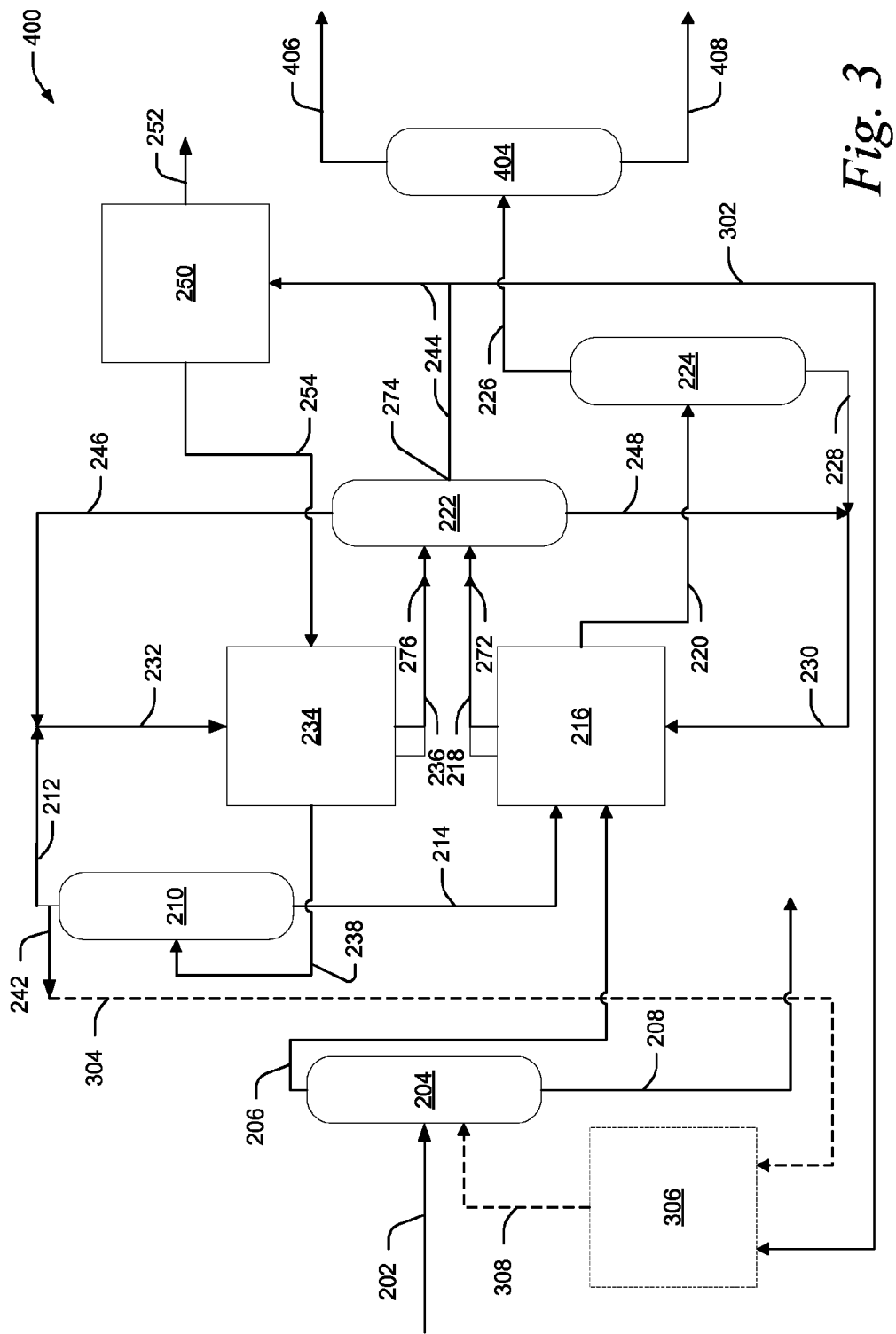
FIG. 3 is a diagram of one embodiment of the disclosed process having an adsorption unit with multiple feeds where a drag stream is fed into an aromatic conversion unit.

Referring to FIG. 3, diagram 300 illustrates one embodiment of Applicant's apparatus and process including an aromatic conversion unit. To prevent accumulation of C9 aromatics in the isomerization loop (i.e., 254, 236, 244), a drag stream 302 is withdrawn from the isomerization loop by way of raffinate stream 244. The drag stream is fed into an aromatic conversion unit 306. All or a portion of the light desorbent slip stream 242, comprising toluene, is directed into the aromatic conversion unit 306 by way of stream 304.

The aromatic conversion unit 306 converts the incoming stream 304 comprising a mixture of toluene and C7− aromatics into an output stream 308 comprising an equilibrium mixture of xylene isomers and ethylbenzene. The aromatic conversion unit 306 facilitates catalytic disproportionation reactions, which convert toluene into a mixture of benzene and xylene isomers. In one embodiment, any C7− aromatics produced are removed from aromatic unit 306 (stream not shown). The aromatic unit 306 also facilitates catalytic transalkylation reactions, which convert a blend of toluene and C9 aromatic isomers to xylene isomers through the migration of methyl groups between methyl-substituted aromatics.

The aromatic conversion product stream 308 enters the xylene fractionation unit 204. The C8− aromatics exit the xylene fractionation unit 204 by way of stream 206. The C9+ aromatics exit the xylene fractionation unit by way of stream 208.

Figure 4:
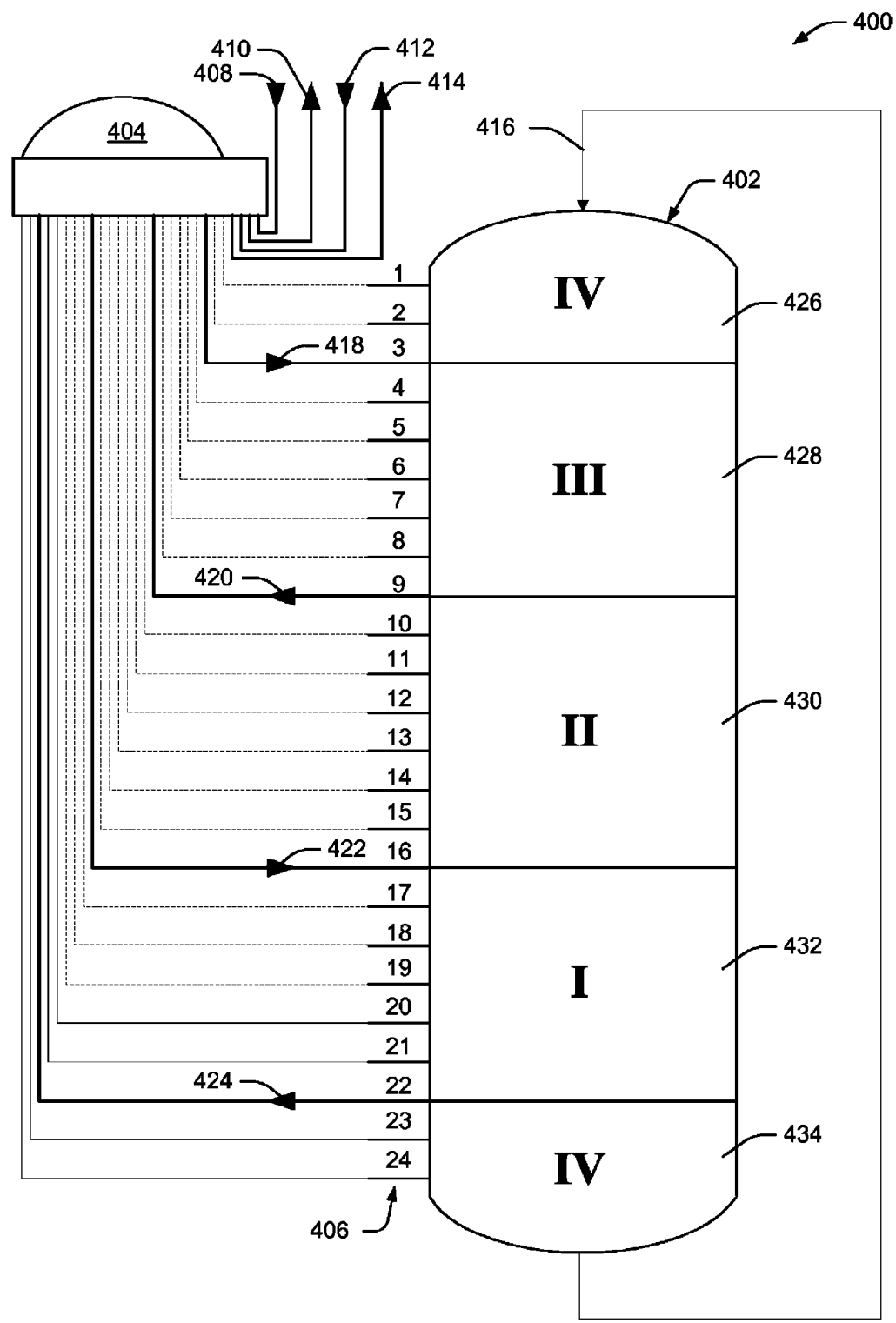
FIG. 4 is a diagram of a prior art adsorptive separation unit.

FIG. 4 illustrates a prior art adsorptive separation unit 400. The unit 400 includes a housing 402. The adsorptive separation unit 400 contains a solid zeolitic adsorbent and a number of beds with corresponding bed lines 406.

As material is fed into the chamber and flows downwardly, the material contacts the solid adsorbent within the chamber. The adsorbent having an affinity for the desired xylene isomer is selected for the chamber. Certain types of zeolitic adsorbents have an affinity for para-xylene. As the feed stream flows over the solid adsorbent, the para-xylene is selectively adsorbed into the adsorbent while the other isomers continue to travel downward in the chamber in the bulk liquid. Material that reaches the bottom of the chamber is reinserted into the top of the chamber by way of recycle line 416 to create a continuous flow of bulk liquid.

While a single chamber 402 is shown, the chamber 402 may be split into two or more individual chambers, with the bottom of a given chamber in fluid communication with the top of another chamber to create a functional equivalent of chamber 402.

A rotary valve 404 controls the flow of material into and out of the bed lines 406 and the net flow of material into and out of the assembly 400 through the assembly inputs and outputs, including feed input 408, raffinate output 410, desorbent input 412, and extract output 414. A feed stream comprising mixed xylene isomers is fed into line 408. A desorbent stream comprising para-diethylbenzene, is fed into the desorbent input 412. An extract stream of high purity para-xylene is withdrawn from extract output 414. A raffinate stream of para-xylene-depleted C8 aromatics is withdrawn from raffinate output 410.

The rotary valve 404 directs the stream of material from each of the assembly inputs and outputs to specific bed lines. The rotary valve has 24 steps, each corresponding to a particular configuration of input and output streams to the bed lines 406. As the rotary valve moves from one step to the next, the streams from the assembly inputs and outputs each move to the next bed line lower on the chamber. For example, at step 1, the raffinate stream may initially be pulled from bed line 22. In subsequent steps 2, 3, and 4, the raffinate stream will be pulled from bed line 23, 24, and 1, respectively. The rotary valve also controls a number of flush lines (not shown) to flush the bed lines of material (i.e., extract, feed, raffinate, or desorbent) from a previous step, using a constant flush line flow, to prepare the bed lines for a future step (i.e., desorbent, extract, feed, and raffinate, respectively).

The routing of the assembly input and output streams by the rotary valve 404 to the chamber 402 for step=n is shown in FIG. 4. In the interest of clarity, the streams were equally distributed along the heights of chamber 402 in FIG. 4. The feed stream 422 is routed to bed line 16, the raffinate stream 424 is routed from bed line 22, the desorbent stream 418 is routed to bed line 3, and the extract stream 420 is routed from bed line 9.

The adsorption zone 432 (Zone I) is defined as the portion of the chamber between the feed stream 422 and the raffinate stream 424, where the para-xylene is adsorbed into the solid adsorbent.

The desorption zone 428 (Zone III) is defined as the portion of the chamber between the desorbent stream 418 and the extract stream 420. The desorbent is selected to have approximately the same affinity for solid adsorbent as the desired xylene isomer. As such, the desorbent washes (i.e., desorbs) the adsorbed para-xylene from the solid adsorbent.

The purification zone 430 (Zone II) is defined as the portion of the chamber between the extract stream 420 and the feed stream 422. In the purification zone 430, the higher affinity para-xylene displaces other xylene isomers within the adsorbent back into the bulk solution, thereby flushing the other xylene isomers down the chamber.

The buffer zone 426 and 434 (Zone IV) is defined as the portion of the chamber between the raffinate stream 424 and the desorbent stream 418. The buffer zone 426/434 allows the undesired xylene isomers (i.e., ortho- and meta-xylene) to be extracted by the raffinate stream before the extraction of the desired xylene isomer (i.e., para-xylene) is initiated by the desorbent stream 418.

As the rotary valve advances to step n+1, the position of the desorbent stream 418 transitions from bed line 3 to bed line 4, the position of the extract stream 420 transitions from bed line 9 to bed line 10, the position of the feed stream 422 transitions from bed line 16 to bed line 17, and the position of the raffinate stream 424 transitions from bed line 22 to bed line 23. The streams transition in similar fashion for each subsequent set n+2 to n+23, after which the rotary valve returns to step=n as shown in FIG. 4.

Figure 5:
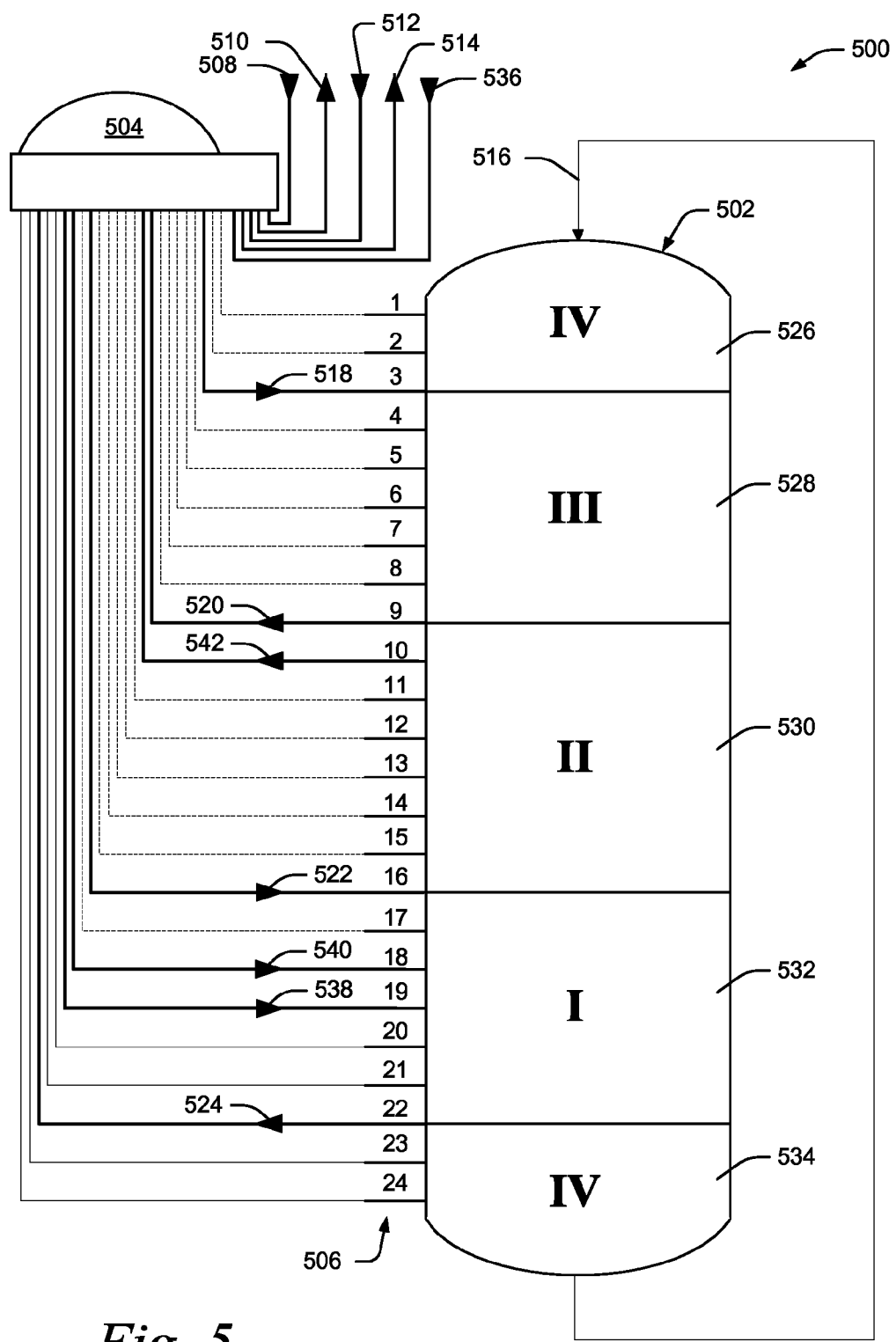
FIG. 5 is a diagram of one embodiment of an adsorptive separation unit having multiple feeds and dynamic flushing.

Referring to FIG. 5, a diagram illustrates one embodiment of Applicant's adsorptive separation assembly 500. The assembly 500 comprises an adsorption chamber 502. In one embodiment, the adsorption chamber 502 contains a solid zeolitic adsorbent and a number of beds with corresponding bed lines 506. The number of beds may vary.

As material is fed into the chamber and flows downwardly, the material contacts the solid adsorbent within the chamber. The adsorbent with the an affinity for the desired xylene isomer is selected for the chamber. Para-xylene isomer has a particular affinity for certain types of zeolitic adsorbents. As the feed stream flows over the solid adsorbents, the para-xylene is selectively adsorbed into the adsorbent while the other isomers continue to travel downward in the chamber. Material that reaches the bottom of the chamber is reinserted into the top of the chamber by way of recycle line 516 to create a continuous flow of material.

In one embodiment, the chamber 502 is a single physical chamber. In one embodiment, the physical chamber includes 24 beds. In one embodiment, the physical chamber includes less than 24 beds. In one embodiment, the chamber 502 includes two or more physical chambers. In one embodiment, each physical chamber includes 12 beds. In one embodiment, each physical chamber includes less than 12 beds. In one embodiment, each physical chamber includes more than 12 beds. In one embodiment, the physical chambers have an unequal number of beds. In different embodiments, the chamber 502 includes more than two physical chambers.

In one embodiment, a rotary valve 504 controls the flow of material into and out of the bed lines 506 and the net flow of material into and out of the assembly 500 through the assembly inputs and outputs, including primary feed input 508, secondary feed input 536, raffinate output 510, desorbent input 512, and extract output 514. In different embodiments, one or more rotary valves, one or more computing device operated valves, or a combination thereof controls the flow of material into and out of the bed lines 506 and the net flow of material into and out of the assembly 500. A primary feed stream is fed into primary feed input 508. A secondary feed stream, having a lower concentration of para-xylene than the primary feed stream, is fed into secondary feed input 536. A desorbent stream, is fed into the desorbent input 512. An extract stream is withdrawn from extract output 514. A raffinate stream is withdrawn from raffinate output 510.

In one embodiment, the feed stream comprises mixed xylene isomers. In different embodiments, the feed stream comprises mixed xylene isomers as well as heavy impurities, light impurities, or a combination thereof. In one embodiment, the extract stream comprises high purity para-xylene. In one embodiment, the raffinate stream comprises ortho- and para-xylene. In one embodiment, the desorbent stream comprises para-diethylbenzene. In certain embodiments, the desorbent stream comprises a desorbent selected from the group consisting of para-diethylbenzene, para-diisopropylbenzene, tetralin, and the like, and combinations thereof. In one embodiment, the desorbent stream comprises toluene. In one embodiment, the desorbent stream comprises a desorbent other than toluene.

In one embodiment, a line connects each bed line on chamber 502 with a different port on the rotary valve. In one embodiment, 10 of such lines have material actively flowing during operation while the material in the other 14 lines are stagnant. In one embodiment, greater than 10 of such lines have material actively flowing during operation while the material in the remaining lines are stagnant. The active lines are used to direct a stream of material from each of the assembly inputs and outputs to specific bed lines (4 lines), flush certain input and output lines in a non-dynamic fashion (4 lines), and flush other input and output lines in a dynamic fashion (2 lines).

In one embodiment, the rotary valve has 24 steps, each corresponding to a particular configuration of input and output stream to the bed lines 506. In one embodiment, the number of steps defined by the rotary valve equals the number of beds in chamber 502.

In one embodiment, as the rotary valve moves from one step to the next, the streams from the assembly inputs and outputs move to the next bed line lower on the chamber. For example, at step n, the raffinate stream may initially be pulled from bed line 22. In subsequent steps n+1, n+2, and n+3, the raffinate stream will be pulled from bed line 23, 24, and 1, respectively. The rotary valve also controls a number of flush lines (not shown) to flush the bed lines of material (i.e., extract, feed, raffinate, or desorbent) from a previous step to prepare the bed lines for a future step (i.e., desorbent, extract, feed, and raffinate, respectively).

The rotary valve includes a track for each active stream. Each given track is in constant fluid communication with either an assembly input or output (i.e., 508, 536, 510, 512, or 514) or with an internal flush line. Each given track is also in constant fluid communication with a crossover line. The cross over lines are configured to fluidly connect to a different port at each step of the rotary valve and, as such, connect an assembly input or output or flush line, as the case may be, with a particular bed line.

The routing of the assembly input and output streams by the rotary valve to the chamber 502 for step=n is shown in FIG. 5. In the interest of clarity, the streams 508, 510, 512, and 514 are equally distributed along the height of bed 502. The feed stream 522 is routed to bed line 16, the raffinate stream 524 is routed from bed line 22, the desorbent stream 518 is routed to bed line 3, and the extract stream 520 is routed from bed line 9.

The adsorption zone 532 (Zone I) is defined as the portion of the chamber between the feed stream 522 and the raffinate stream 524, where the para-xylene in the feed stream is adsorbed into the solid adsorbent.

The desorption zone 528 (Zone III) is defined as the portion of the chamber between the desorbent stream 518 and the extract stream 520. The desorbent is selected to have approximately the same affinity for solid adsorbent as the desired xylene isomer. As such, the desorbent washes (i.e., desorbs) the adsorbed para-xylene from the solid adsorbent in the desorption zone 528.

The purification zone 530 (Zone II) is defined as the portion of the chamber between the extract stream 520 and the feed stream 522. In the purification zone 530, the higher affinity para-xylene displaces other xylene isomers within the adsorbent back into the bulk solution, thereby flushing the other xylene isomers down the chamber.

The buffer zone 526 and 534 (Zone IV) is defined as the portion of the chamber between the raffinate stream 524 and the desorbent stream 518. The buffer zone 526 allows the undesired xylene isomers (i.e., ortho- and meta-xylene) to be extracted by the raffinate stream before the extraction of the desired xylene isomer (i.e., para-xylene) is initiated by the desorbent stream 518.

In one embodiment, the secondary feed stream 538, having a lower concentration of para-xylene than the primary feed stream 522, is introduced into the chamber within the adsorption zone 532. The concentration of para-xylene in the bulk liquid within the adsorption zone 532 (i.e., the liquid flowing downward within the chamber) decreases as the para-xylene is adsorbed into the solid adsorbent. The concentration in the bulk liquid in adsorption zone 532 has a maximum concentration of para-xylene at feed point 522 and a minimum concentration at raffinate point 524. In one embodiment, the secondary feed stream 538 is fed into a bed line on chamber 502 within the adsorption zone where the concentration of para-xylene within the chamber at the point of such bed line is nearest the composition of para-xylene in the secondary feed stream.

At the step=n state depicted in FIG. 5, bed lines 17 and 18, as well as the volume of the line connecting bed lines 17 and 18 with the rotary valve and the corresponding volume internal to the rotary valve, contain secondary feed liquid from the previous step=n−2 and step=n−1, respectively. In one embodiment, at the beginning of the step=n state depicted in FIG. 5, a portion of primary feed stream 522 is directed into primary flush line 540. As a result, the secondary feed liquid in the primary flush line 540 is driven into the chamber and the primary flush line is backfilled with primary feed liquid.

In one embodiment, the primary flush stream 540 is fed into a bed line on chamber 502 where the concentration of para-xylene within the chamber at the point of such bed line is nearest the composition of para-xylene in the secondary feed stream. At the previous step (i.e., step=n−1), the secondary feed stream 538 was fed into bed line 18. As such, the concentration of para-xylene in the chamber at bed line 18 at the beginning of step=n is very close to that of the secondary feed stream 538. As the step=n progresses, the concentration profile within the adsorption zone 532 shifts downward and the concentration of para-xylene at bed line 18 increases as the bulk liquid, richer in para-xylene from primary feed stream 522, flows downward.

By forcing any secondary feed liquid within the primary flush line 540 (as well as any liquid in the rotary valve and lines connected to the primary flush line 540 filled with secondary feed liquid) rapidly at the beginning of step=n, the concentration profiles between the secondary feed liquid and that within the chamber are best matched. Matching the concentration of (i) material introduced into the chamber 502 with (ii) the concentration at the introduction point prevents concentration spikes in the chamber. Such spikes interfere with the operation of the chamber, reducing efficiency and disrupting the constant composition of extract stream 514.

In one embodiment, the volume of the primary feed stream 522 directed into the primary flush stream 540 matches the combined volume of the bed line 18, the associated distributor piping within the chamber, the line connecting the bed line with the rotary valve, and the volume within the rotary valve for the primary flush stream 540. In one embodiment, because such volume may differ for each step as a result of the pipes and lines connecting the various locations on the chamber with the rotary valve and the tracks within the rotary valve, the volume of the primary feed stream 522 directed into the primary flush 540 is sufficient to fully flush the bed line and associated distributor piping, the line connecting the bed line with the rotary valve, and the volume within the rotary valve for the step position (step=n to step=n+23) having the greatest volume. In one embodiment, the volume of the primary feed stream 522 directed into the primary flush 540 is sufficient to flush the line connecting the bed line with the rotary valve, and the volume within the rotary valve for the step position (step=n to step=n+23) having the smallest volume. In one embodiment, the volume of the primary feed stream 522 directed into the primary flush stream 540 is sufficient to flush a portion of the secondary feed liquid from the bed line 18. In one embodiment, the volume of the primary feed stream 522 directed into the primary flush stream 540 is sufficient to substantially flush (i) the rotary valve track and (ii) the line connecting the rotary valve leading to bed line 18.

At the step=n state depicted in FIG. 5, bed lines 10-15, as well as the volume of the line connecting bed lines 10-15 with the rotary valve and the corresponding volume internal to the rotary valve, contain primary feed liquid from the previous step=n−6 to step n−1, respectively. At the end of the step=n state, a secondary flush stream 542 is withdrawn from the purification zone 530 and combined with the primary feed stream 522 by way of stream 624. In one embodiment, the secondary flush stream 542 is combined with the primary feed stream 522 within the rotary valve. In one embodiment, the secondary flush stream 542 is combined with the primary feed stream 522 before the primary feed stream 522 enters the rotary valve.

In one embodiment, the secondary flush stream 542 is withdrawn from a bed line on chamber 502 within the purification zone 530 where the concentration of para-xylene within the chamber at the point of such bed line is nearest the composition of para-xylene in the extract stream 520. As a result, the primary feed liquid initially in bed line 10 is flushed into in the chamber 502 at the primary feed point 522 and the primary feed stream is backfilled with liquid similar in para-xylene concentration to that of extract stream 520. At step=n+1 through step=n+6, bed lines 10 through 15, respectively, are used to remove extract streams, and will have already been preloaded with liquid similar in composition to the extract stream.

In one embodiment, the volume of the secondary flush stream 542 directed into the primary feed stream 522 matches the combined volume of the bed line 16, the volume of piping in the rotary valve, and the volume of distributor piping to chamber 502. In one embodiment, because such volume may differ for each step as a result of difference in the bed line piping and tracks within the rotary valve, the volume of the secondary flush stream 542 directed into the primary feed 522 is sufficient to fully flush the bed line such related piping for the step position (step=n to step=n+23) having the greatest volume. In one embodiment, the volume of the secondary flush stream 542 directed into the primary feed 522 is sufficient to fully flush the bed line such related piping for the step position (step=n to step=n+23) having the smallest volume. In one embodiment, the volume of the secondary flush stream 542 directed into the primary feed stream 522 is sufficient to flush a portion of the primary feed liquid from the bed line 16 and preload a portion of the bed line or related piping with material similar in composition to the extract stream 520. In one embodiment, the volume of the secondary flush stream 542 directed into the primary feed stream 522 is sufficient to substantially flush (i) the piping in the rotary valve and (ii) the distributor piping connecting the rotary valve to bed line 16.

In one embodiment, the adsorptive separation assembly is used in the process of FIG. 2 as adsorptive separation unit 216. In such embodiment, primary feed input 508 corresponds to the first feed input 278 and stream 214 in FIG. 2. The secondary feed input 536 corresponds to the second feed input 280 and stream 206 in FIG. 2. The raffinate output 510 corresponds to stream 218 in FIG. 2. The desorbent input 512 corresponds to stream 230 in FIG. 2. And, the extract output 514 corresponds to stream 220 in FIG. 2.

Figure 6:
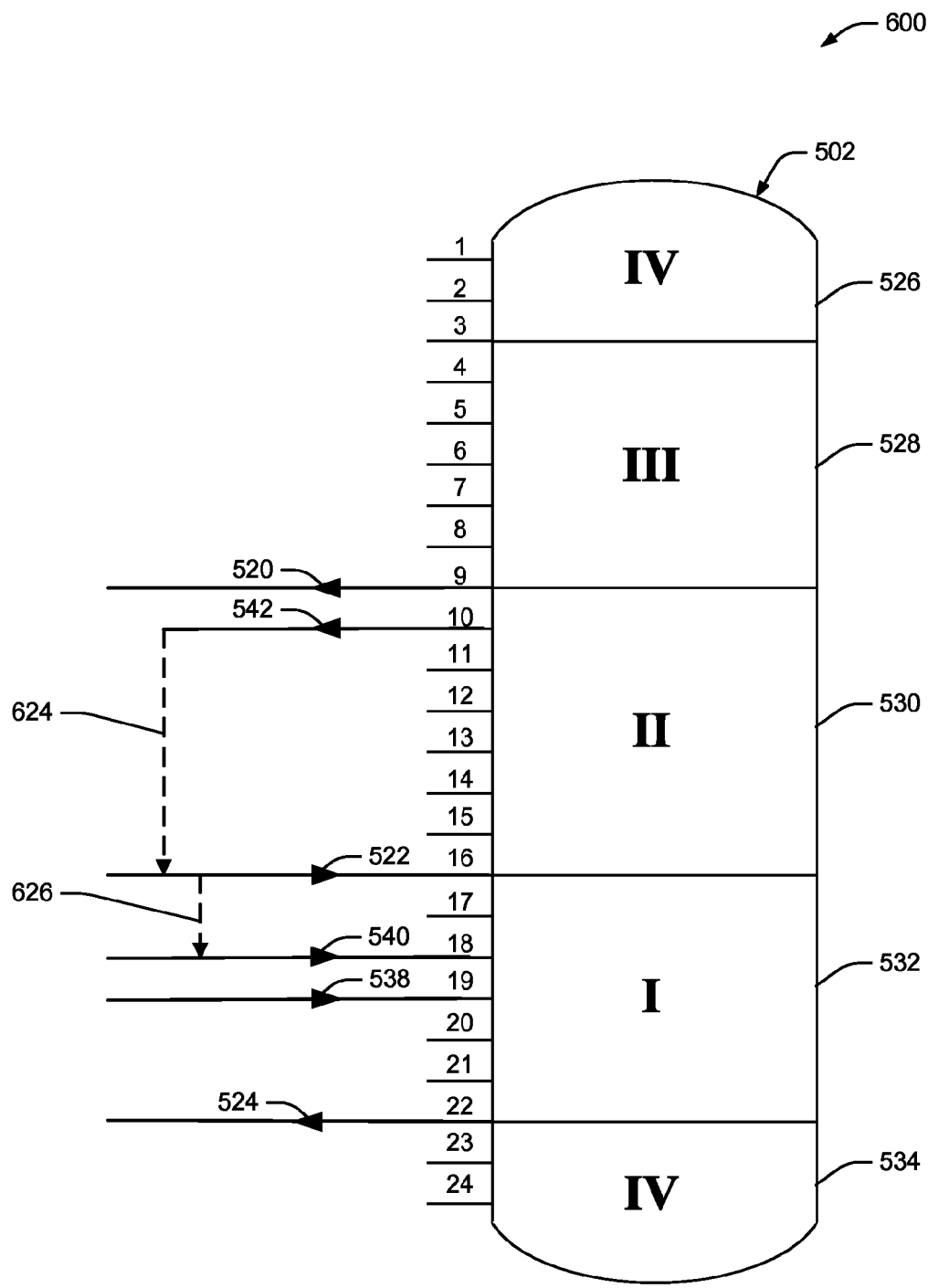
FIG. 6 is a simplified diagram of one embodiment of Applicants' adsorptive separation unit having multiple feeds and dynamic flushing.

Referring to FIG. 6, a simplified diagram 600 of one embodiment of Applicant's multi-feed column is depicted. The rotary valve, non-active lines, and an active line have been omitted for purposes of clarity. The configuration in FIG. 6 is at step=n.

At step=n, the primary feed stream 522 is introduced into bed line 16, the raffinate stream 524 is withdrawn from bed line 22, and the extract stream 520 is withdrawn from bed line 9.

At the beginning of step=n, a portion of the primary feed stream 522 is fed into a primary flush stream 626 to flush the existing material (i.e., the secondary feed liquid from the last use of the bed line) into stream 540, through the volume of bed line 18, the volume of piping in the rotary valve, and the volume of distributor piping internal to chamber 502. In one embodiment, the primary flush happens rapidly at the beginning of the step=n.

After the primary flush is complete, the bed line 18, the volume of piping in the rotary valve, and the volume of distributor piping to the chamber 502 are preloaded with material similar in composition to the primary feed stream. At step=n+2, when bed line 18 is used for the primary feed stream, the bed line 18, the volume of piping in the rotary valve, and the volume of distributor piping to the chamber 502 will have a para-xylene concentration matching that within the chamber at bed line 18.

Toward the end of step=n, a secondary flush stream 542 is rapidly withdrawn from bed line 10 in the purification zone 530. The flush completes before the rotary valve transitions to the next step (i.e., step=n+1). Bed line 10 is adjacent to extract bed 9 and, as such, the material in the chamber 502 at bed line 9 and bed line 10 are similar in para-xylene concentration.

At the beginning of step=n+1, in one embodiment, the primary feed material, initially in bed line 16, has been flushed into the chamber 502 and the bed line and related piping have been preloaded with material similar in composition to the extract material stream. In addition, bed line 10 has also been flushed of primary feed material and preloaded with material similar in composition to the extract material stream. At step=n+1, the extract stream flows through bed line 10. At step=n+6, the extract stream flows through bed line 16.

Figure 7:
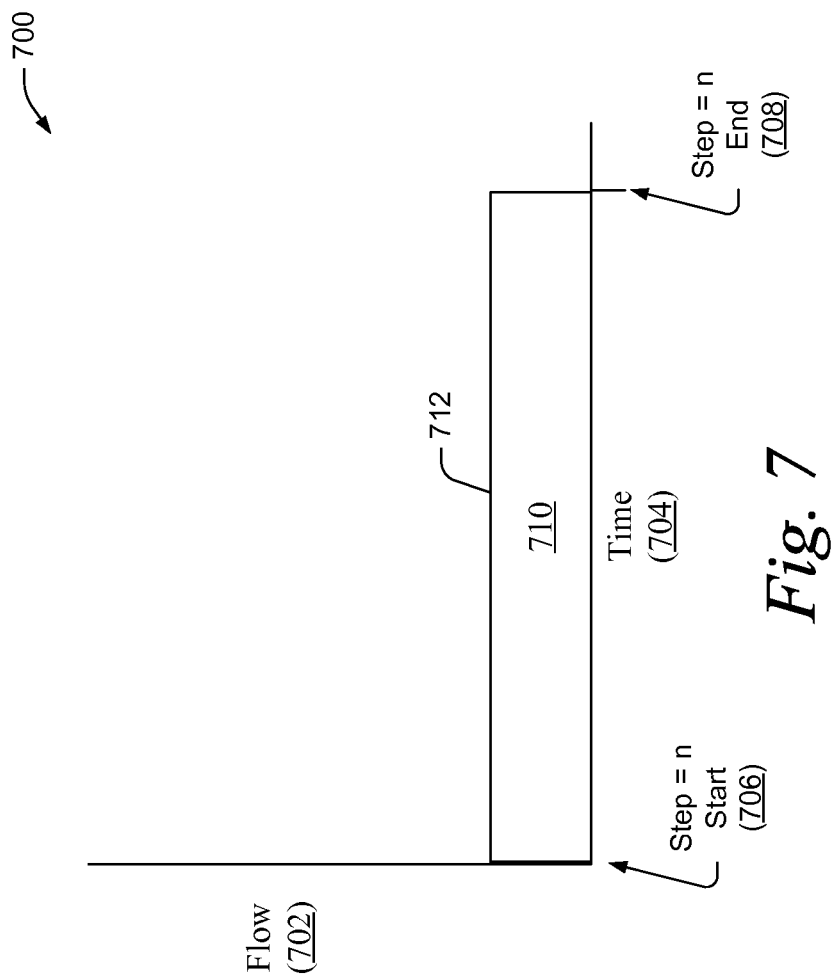
FIG. 7 is a chart showing the flush profile of the prior art.

FIG. 7 graphically illustrates a flow profile as a function of time for a prior art flush. The step-time interval 704 on the x-axis represents the time for a full step interval. The step starts at 706 and ends at 708. The y-axis represents the flow rate and the curve 712 represents the flow rate of the flush at each point in time from the start 706 to the end 708. The area 710, represents the total flush volume for the step interval. The flow rate depicted in graph 700 is constant and uniform for the entirety of the step interval.

FIG. 8(a) graphically illustrates an exemplary flow profile as a function of time for a primary flush used in Applicant's system. The step-time interval 808 on the x-axis 804 represents the time for a full step interval. The step starts at 806 and ends at 808. The y-axis 802 represents the flow rate and the curve 812 represents the flow rate of a primary flush at each point in time from the start 806 to the end 808. The area 810, represents the total flush volume for the step interval. The flow rate shown in graph 800 is front-loaded such that substantially all the flush volume occurs toward the beginning of the step interval and drops off rapidly, in one embodiment, at about the step mid-point 814.

FIG. 8(b) graphically illustrates an exemplary flow profile as a function of time for a secondary flush used in Applicant's system. The step-time interval 808 on the x-axis 804 represents the time for a full step interval. The step starts at 806 and ends at 808. The y-axis 802 represents the flow rate and the curve 862 represents the flow rate of the flush at each point in time from the start 806 to the end 808. The area 860, represents the total flush volume for the step interval. The flow rate depicted in graph 850 is back-loaded such that substantially all the flush volume begins, in one embodiment, at about the midpoint 805 and ends at time 808.

In one embodiment, the primary flush drops to about zero flow at or before midpoint 805. In one embodiment, the secondary flush initiates at or after midpoint 805. In certain embodiments, there is no flow overlap between curve 812 and curve 862, i.e., the primary flush and secondary flush each have zero flow rate at midpoint 805. In other embodiments, the primary flush and secondary flush each have a flow rate greater than zero at midpoint 805.

Figure 9:
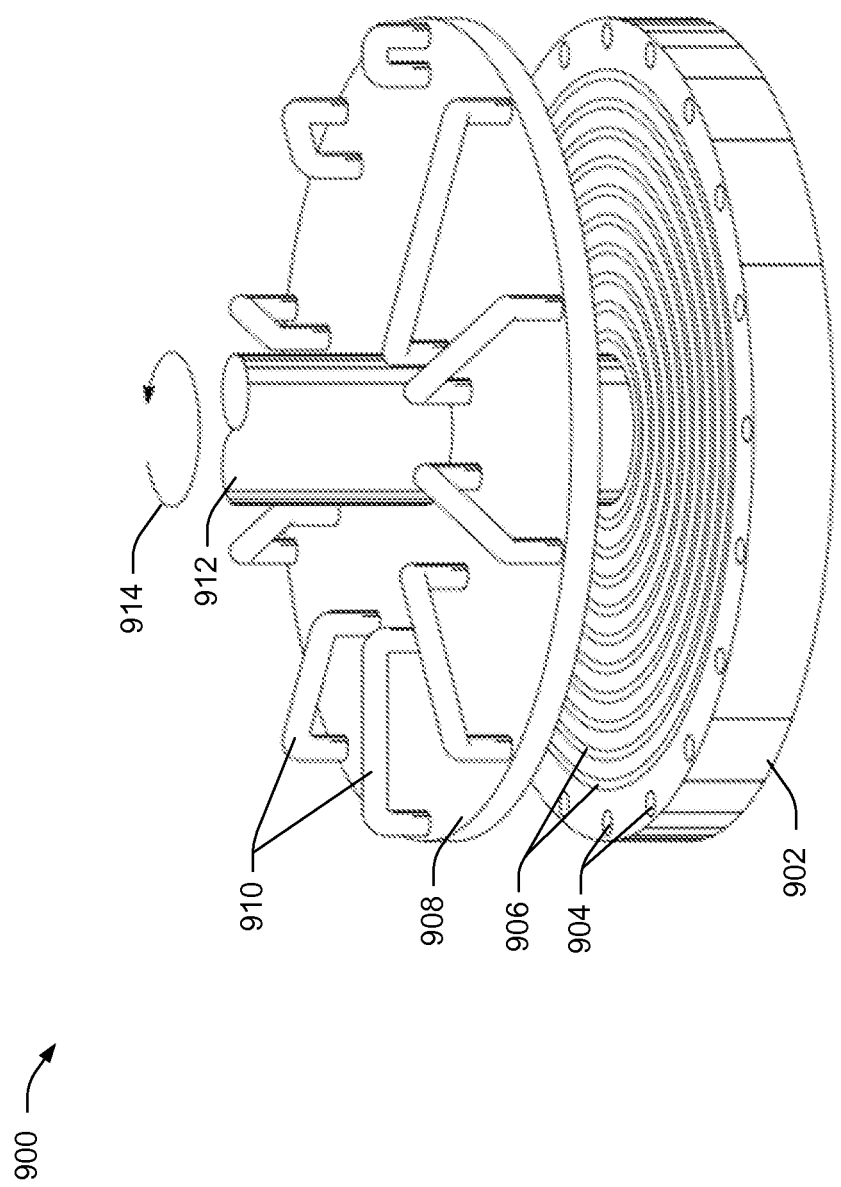
FIG. 9 is a diagram of one embodiment of a rotary valve for use in Applicant's apparatus and process.

Referring to FIG. 9, a simplified exploded diagram of one embodiment of a rotary valve 900 for use in Applicant's multi-teed adsorptive separation unit is depicted. A base plate 902 includes a plurality of ports 904. The number of ports 904 is equal the total number of bed lines on the SMB chamber(s). The base plate 902 also includes a plurality of tracks 906. The number of tracks 906 is equal the number of net input, output, and flush lines for the adsorptive separation unit.

The net inputs, outputs, and flush lines are each in fluid communication with a different track of the plurality of tracks 906. Crossover lines 910 place a given track 906 in fluid communication with a given port 904. As the rotor plate 908 rotates as indicated by arrow 914, each track 906 is placed in fluid communication with the next successive port 904 by crossover line 910. As such, the rotary valve 900 ports each of the net inputs, outputs, and flush lines to a different port 904. With each full rotation of the rotor plate 908, a given input, output, or flush line will have been routed to each of the ports 904.

In one embodiment, the net inputs include a primary feed input, a secondary feed input, and a desorbent input, the net outputs include an extract output and a raffinate output, and the flush lines include two constant flow flush lines and three dynamic flow flush lines. In this embodiment, the rotary valve comprises 10 tracks, as depicted in FIG. 9.

In another embodiment, the net inputs include a primary feed input, a secondary feed input, and a desorbent input, the net outputs include an extract output and a raffinate output, and the flush lines include two constant flow flush lines and two dynamic flow flush lines. In this embodiment, the rotary valve comprises 9 tracks. As would be apparent to those skilled in the art, rotary valves of less than 9 tracks and greater than 10 tracks could be constructed in similar fashion by adding or removing tracks and associated crossover lines accordingly.

Figure 10:
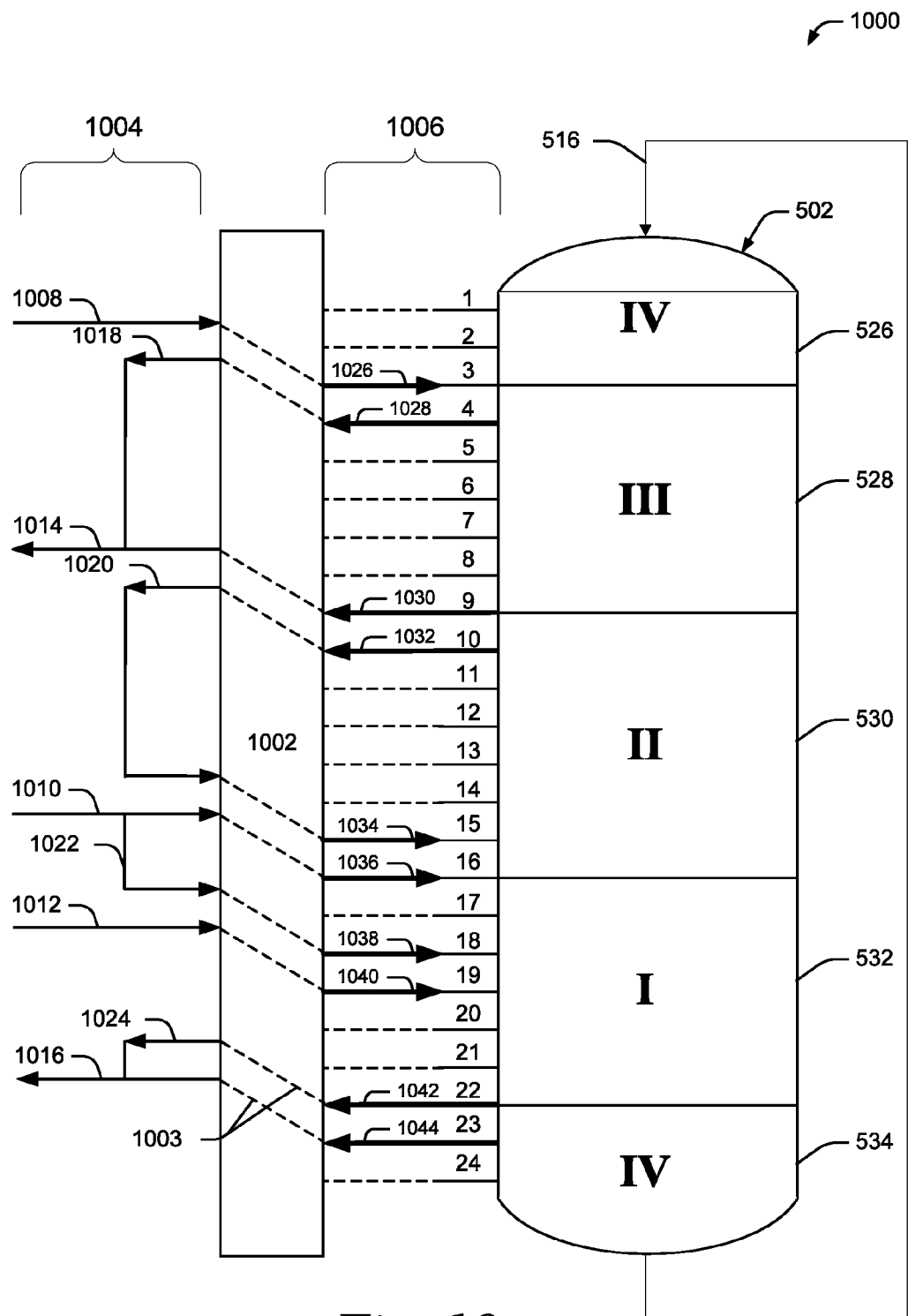
FIG. 10 is a diagram of one embodiment of Applicant's adsorption separation assembly having a multi-feed column and a ten track rotary valve.

Referring to FIG. 10, a diagram of an embodiment of Applicant's adsorption separation assembly 1000 having a multi-feed column and a ten (10) track rotary valve is depicted. The assembly 1000 comprises an adsorption chamber 502 and a rotary valve 1002. The rotary valve 1002 is represented as a block with ten individual tracks 1003 connecting the stationary lines 1004 with certain bed lines 1006. The rotary valve is shown in the step=n configuration. As the rotary valve advances to the step=n+1, the tracks shift downward such that the stationary lines 1004 are connected with the next bed line 1006 down the adsorption chamber 502. For example, a track connecting an input with bed line 23 at step=n, will connect the input to bed line 24 at step=n+1 and bed line 1 at step=n+2.

Three input streams, a desorbent stream 1008, a primary feed stream 1010, and a secondary feed stream 1012, feed material into the rotary valve. Two output streams, an extract stream 1014 and a raffinate stream 1016, receive material from the rotary valve. A number of flush lines, 1018, 1020, 1022, and 1024, recirculate material in preparation for upcoming steps.

The extract flush line 1018 (i) flushes extract material from the distribution line 1026 that was last used as an extract output and (ii) loads the distribution line 1026 with material similar in composition to the desorbent stream 1008. As used herein, the usage "bed line 1026" refers to the physical bed line on the outside of chamber 502. Whereas, the usage "distribution lines 1026" refers to the volume within the physical bed line 1026 external to chamber 502, the distributor piping within chamber 502 connected to bed line 1026, and the channels through rotary valve 1002 connected to bed line 1026.

The material in the distribution line 1026 is loaded with high purity para xylene material. As such, reintroduction of high purity para-xylene into chamber 502 when the bed line is later used as a desorbent input, which would disrupt the separation process within the chamber, is avoided.

During the extract flush, material is withdrawn by way of extract flush bed line 1028, a bed line below the desorbent bed line 1026 on chamber 502. In one embodiment, bed line 1028 is directly adjacent to the desorbent bed line 1026. In one embodiment, the bed line 1028 is separated from desorbent bed line 1026 by at least one bed line. As such, the material loaded into the distribution line is similar in composition to the desorbent stream 1008.

The distribution line was last used as an extract output. As such, the material flushed out of the distribution line comprises extract material from a previous rotary step. In one embodiment, the flushed material is combined with extract stream 1014.

In one embodiment, the amount of material pulled from the chamber 502 into the distribution line 1028 is substantially the same as the volume of the distribution line 1028 and extract flush line 1018. In one embodiment, the amount of material pulled from the chamber 502 into the bed line and associated distributor piping is less than the volume of the distribution line 1028 and extract flush line 1018.

A primary flush line 1020 flushes feed material from the upper portion of purification zone 530 to the lower portion of purification zone 530. Distribution line 1032, which serves as the primary flush out, was most recently used in a previous step as the primary flush in. Before the primary flush, in one embodiment, the material within distribution line 1032 comprises material similar in composition to the exact stream 1014.

Distribution line 1034, which serves as the primary flush in, was most recently used in a previous step as the primary feed input. Before the primary flush, the material within distribution line 1034 comprises primary feed material.

The primary flush line 1020 loads material from a location on the chamber 502 proximate the extract bed line 1030 into primary flush out distribution line 1032. In one embodiment, the primary flush out bed line 1032 is directly adjacent to the extract bed line 1030. In one embodiment, the primary flush out bed line 1032 is separated by the extract bed line 1030 by at least one bed line.

Material previously in distribution line 1034 is flushed into the chamber 502 at a location proximate the primary feed input bed line 1036. In one embodiment, the primary flush in bed line 1034 is directly adjacent to the primary feed input bed line 1036. In one embodiment, the primary flush in bed line 1034 is separated by the primary feed input bed line 1036 by at least one bed line.

Figure 8:
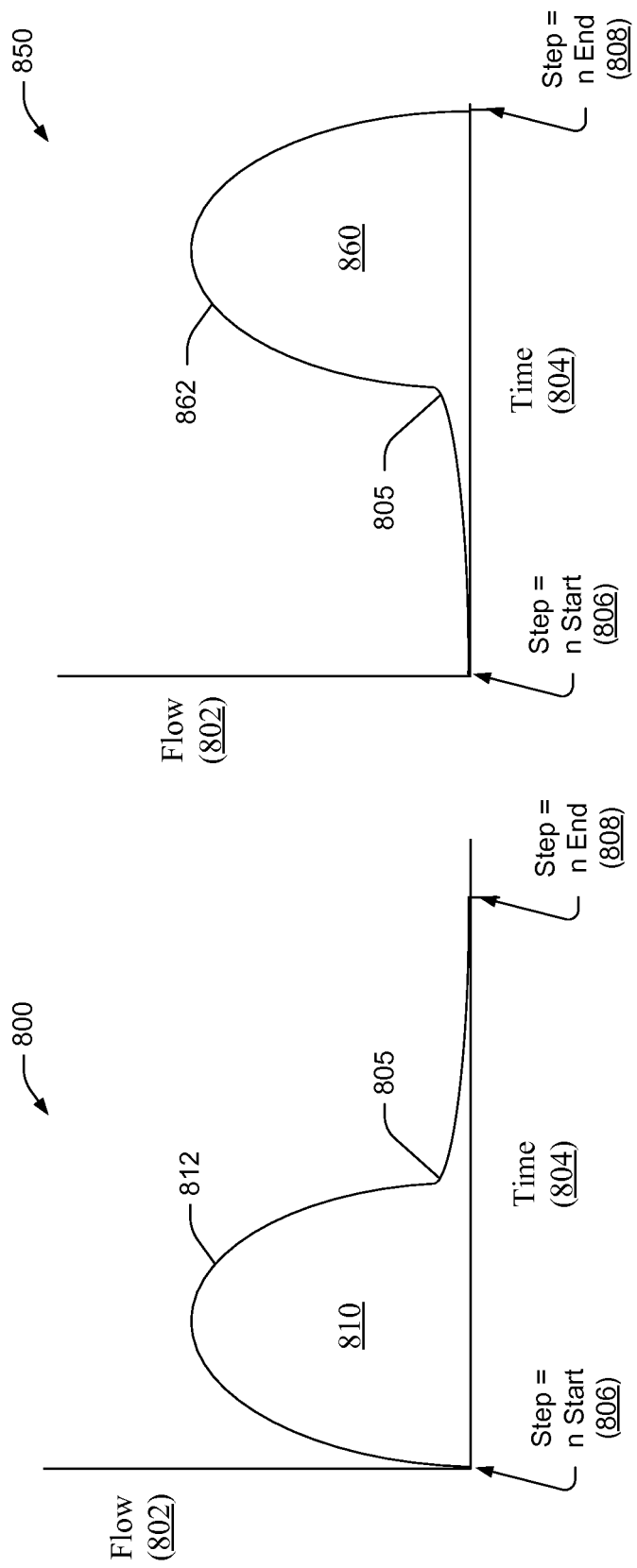
FIGS. 8($a$) and 8($h$) are charts showing the dynamic flush profile used with Applicant's adsorptive separation unit having multiple feeds.

In one embodiment, the primary flush is non-uniform, having a flow profile similar to that depicted in FIG. 8(*b*). In one embodiment, the primary flush is non-uniform, having a flow profile similar to that depicted in FIG. 8(*a*). In one embodiment, the primary flush has a uniform flow profile throughout the rotary valve step. In one embodiment, the amount of material pulled from the chamber 502 into the distribution line 1032 is substantially the same as the volume of distribution line 1032. In one embodiment, the amount of material pulled from the chamber 502 into the distribution line 1032 is greater than the volume of distribution line 1032. In one embodiment, the amount of material pulled from the chamber 502 into the distribution line 1032 is substantially the same as the volume of distribution line 1032 and primary flush line 1020 in one embodiment, the amount of material pulled from the chamber 502 into the distribution line 1032 is greater than the volume of distribution line 1032 and primary flush line 1020. As such, the primary flush out distribution line 1032 is loaded with material similar to the extract stream 1014, thereby avoiding the introduction of a quantity of feed material into the extract stream 1014.

The feed flush line 1022 (i) flushes remaining secondary feed material from a previous step into the chamber 502 and (ii) loads the distribution line with primary feed material for an upcoming step. A portion of the primary feed stream 1010 is diverted into the feed flush distribution line 1038 by way of feed flush line 1022. The distribution line 1038 was more recently used in a previous step as a secondary feed line. As such, the material within distribution line 1038, before the feed flush, comprises secondary feed material. The distribution line 1038 will be used next as the primary feed input. The feed flush line 1022 loads the distribution line 1038 with primary feed material and drives any remaining secondary feed material into the chamber 502.

In one embodiment, the feed flush bed line 1038 is directly adjacent to the secondary feed bed line 1040. In one embodiment, the feed flush bed line 1038 is separated from the secondary feed bed line 1040 by at least one bed line.

In one embodiment, the feed flush is non-uniform, having a flow profile similar to that depicted in FIG. 8(*a*). In one embodiment, the feed flush is non-uniform, having a flow profile similar to that depicted in FIG. 8(*b*). In one embodiment, the feed flush has a uniform flow profile throughout the rotary valve step.

A raffinate flush line 1024 flushes raffinate material in the raffinate flush distribution line 1042, from the most recent step, into the raffinate stream 1016. The raffinate flush loads the raffinate flush distribution line 1042 with material higher in para-xylene content than is present in the raffinate stream 1016. As such, during the next use of the bed line 1042, for secondary feed input, the material in the distribution line 1042 will be more similar in composition to the secondary feed input.

Figure 11:
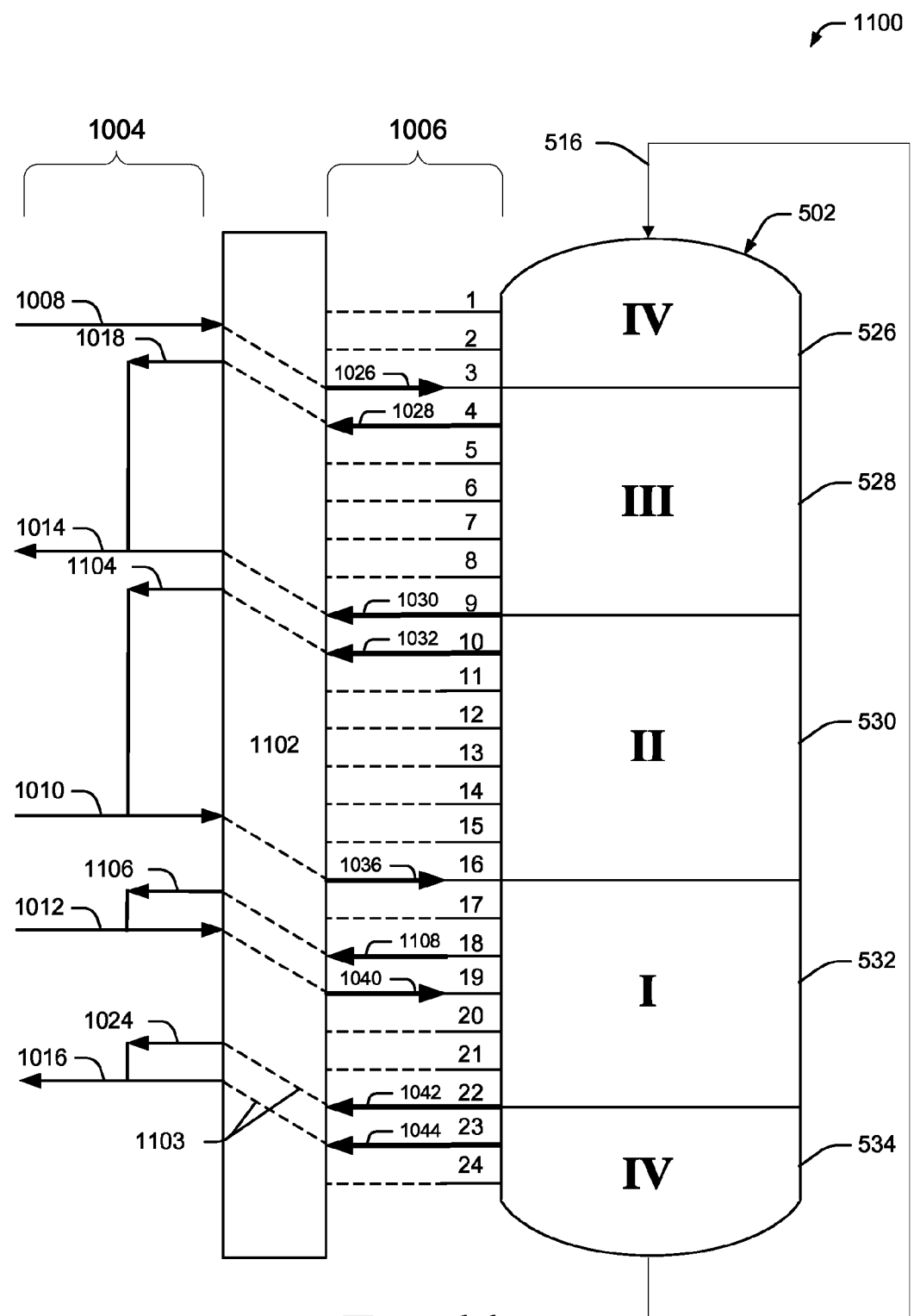
FIG. 11 is a diagram of one embodiment of Applicant's adsorption separation assembly having a multi-feed column and a nine track rotary valve.

Referring to FIG. 11, a diagram of an embodiment of Applicant's adsorption separation assembly 1100 having a multi-feed column and a nine (9) track rotary valve is depicted. The assembly 1100 comprises an adsorption chamber 502 and a rotary valve 1102. The rotary valve 1102 comprises nine individual tracks 1103.

Extract flush 1018 and raffinate flush 1024 operate in the same manner as described in FIG. 11. Primary flush 1104 operates in the same manner as stream 624 as described in FIG. 6. Feed flush 1106 flushes secondary feed material, originally in distribution line 1108 from the most recent step, into the secondary feed stream 1012. Feed flush 1106 also loads distribution line 1108 with material having a higher concentration of para-xylene than is present in the secondary feed stream 1012, in preparation for a future step where bed line 1108 is used as a primary feed input.

In one embodiment, the primary flush 1104 is non-uniform, having a flow profile similar to that depicted in FIG. 8(*a*). In one embodiment, the primary flush 1104 is non-uniform, having a flow profile similar to that depicted in FIG. 8(b). In one embodiment, the primary flush 1104 has a uniform flow profile throughout the rotary valve step. In one embodiment, the embodiment depicted in FIG. 11 is used to implement the flow diagram depicted in FIG. 6.

Each of the disclosed processes avoids the vaporization of the isomerization product stream to extract C9 aromatic impurities. As such, the disclosed processes consume substantially less energy, resulting in lower operational expenditures, and require an overall reduction in equipment costs, resulting in substantially lower capital expenditures, as compared to prior art xylene production processes.

Referring to the foregoing paragraphs, this invention is described in preferred embodiments in the following description with reference to the Figures, in which like numerals represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the above description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

While the invention is described through the above-described exemplary embodiments, it will be understood by those of ordinary skill in the art that modifications to, and variations of, the illustrated embodiments may be made without departing from the inventive concepts disclosed herein. For example, although some aspects of separating para-xylene has been described, those skilled in the art should readily appreciate that functions, operations, decisions, etc., of all or a portion of each step, or a combination of steps, of the series of steps described may be combined, separated into separate operations or performed in other orders. Moreover, while the embodiments are described in connection with various illustrative processes, one skilled in the art will recognize that the methods and processes described herein can be embodied using a variety of techniques. Furthermore, disclosed aspects, or portions of these aspects, may be combined in ways not listed above. Accordingly, the invention should not be viewed as being limited to the disclosed embodiment(s). The scope of the invention should be determined with reference to the pending claims along with their full scope or equivalents, and all changes which come within the meaning and range of equivalency of the claims are to be embraced within their full scope.

What is claimed is:

1. A process for separating para-xylene from a plurality of aromatic compounds, the process comprising:
   introducing throughout a first step-time interval a first mixed xylene stream comprising a plurality of xylene isomers into a first feed input on a first adsorptive separation unit comprising a plurality of bed lines, wherein said first adsorptive separation unit comprises a purification zone;
   introducing throughout said first step-time interval a second mixed xylene stream comprising a plurality of xylene isomers into a second feed input on said first adsorptive separation unit;
   during a first portion of said first said step-time interval, introducing material from a feed stream used during said first step-time interval into a bed line not used to deliver a stream into, or to withdraw a stream from, said first adsorptive separation unit during said first step time interval; and
   during a second portion of said first said step-time interval, introducing material from said purification zone into said feed stream used during said first step-time interval.

2. The process of claim 1, wherein said first portion of said first step-time interval differs from said second portion of said first step-time interval.

3. The process of claim 2, wherein a flow rate of said first mixed xylene stream into said first feed input is non-uniform over said first portion of said first step-time interval.

4. The process of claim 3, wherein a flow rate of said feed material into said second bed line is non-uniform over said second portion of said first step-time interval.

5. The process of claim 1, further comprising:
   producing a first para-xylene enriched stream and a first raffinate stream;
   introducing a second mixed xylene feed stream comprising a plurality of xylene isomers into a second adsorptive separation unit to produce a second para-xylene enriched stream and a second raffinate stream; and
   feeding both said first raffinate stream and said second raffinate stream into a raffinate column.

6. The process of claim 5, further comprising:
   producing by said raffinate column a C8 raffinate stream;
   introducing the C8 raffinate stream into an isomerization unit to produce the said second mixed xylene stream.

7. The process of claim 5, wherein:
   the first raffinate stream enters the raffinate column at a first location;
   the C8 raffinate stream exits the raffinate column at a second location;
   the second raffinate stream enters the raffinate column at a third location; and
   wherein the second location is disposed between the first location and the third location.

8. The process of claim 6, further comprising introducing said second enriched para-xylene stream into a second extract column.

9. The process of claim 8, further comprising introducing said first enriched para-xylene stream into a first extract column.

10. The process of claim 8, further comprising generating a xylene product stream from said second extract column without use of a finishing column.

* * * * *